United States Patent [19]

Watson et al.

[11] Patent Number: 5,028,253
[45] Date of Patent: Jul. 2, 1991

[54] **PROCESS FOR CONTROLLING UNDESIRABLE VEGETATION WITH *COLLETOTRICHUM COCCODES* SPORES**

[75] Inventors: Alan K. Watson, Pincourt, Canada; Alan R. Gotlieb, Essex Junction, Vt.

[73] Assignees: The Royal Institution for the Advancement of Learning (McGill Univ.), Quebec, Canada; The Univ. of Vermont and State Agriculturual College, Burlington, Vt.

[21] Appl. No.: 221,605

[22] Filed: Jul. 20, 1988

Related U.S. Application Data

[63] Continuation of Ser. No. 898,788, Aug. 18, 1986, abandoned, which is a continuation of Ser. No. 573,609, Jan. 25, 1984, abandoned.

[51] Int. Cl.$^5$ ............................................. A01N 63/00
[52] U.S. Cl. ............................................ 71/79; 71/65
[58] Field of Search .................................... 71/79, 65

[56] References Cited

U.S. PATENT DOCUMENTS

| | | | |
|---|---|---|---|
| 4,162,912 | 7/1979 | Charadattan | 71/79 |
| 4,390,360 | 6/1983 | Walker | 71/79 |
| 4,718,935 | 1/1988 | Walker et al. | 71/79 |

OTHER PUBLICATIONS

*Chemical Abstracts*, vol. 99 #184604h Malathvakis, 1983.
*American Type Culture Collection* 14 ed., 1980 pp. 282 and 575.
*Plant Disease Reporter*, vol. 60 No. 3 Stevenson et al., Mar. 1976.
*Plant Disease Reporter*, vol. 62, No. 11, Dingley et al., Nov. 1978.

*Primary Examiner*—Richard L. Raymond
*Assistant Examiner*—Raymond Covington
*Attorney, Agent, or Firm*—Cushman, Darby & Cushman

[57] ABSTRACT

There is disclosed a process for controlling undesirable vegetation, especially velvetleaf by applying *Colletotrichum coccodes* spores onto the undesirable vegetation or onto the situs of the undesirable vegetation. The composition including the fungus spores in an agricultural carrier as well as the growing of the fungus on solid or liquid media are also disclosed. The spores germinate, infect the undesirable vegetation and result in a pathogenic disease which kills or reduces the growth of this undesirable plant.

11 Claims, No Drawings

PROCESS FOR CONTROLLING UNDESIRABLE VEGETATION WITH *COLLETOTRICHUM COCCODES* SPORES

This is a continuation of our prior application Ser. No. 898,788 filed Aug. 18, 1986, which in turn is a continuation of our earlier application Ser. No. 573,609 filed Jan. 25, 1984, both of which applications are now abandoned.

BACKGROUND OF INVENTION (a) Field of the Invention

This invention relates to a process and a composition for controlling undesirable vegetation. More particularly, the present invention is directed to a process for controlling the growth of velvetleaf by applying Colletotrichum spores thereto.

This invention also relates to the growing of a fungus, *Colletotrichum coccodes* (Wallr.) Hughes, collecting spores, concentrating the spores and formulating the spores for application over geographic areas to control undesirable vegetation, namely velvetleaf (*Abutilon theophrasti* Medic.). According to the invention, after application the spores germinate, infect the velvetleaf and result in a pathogenic disease which terminates or reduces the growth of the undesirable plant.

(b) Description of Prior Art

Velvetleaf, often called button-weed or elephant-ear, is an erect annual broadleaf plant species from 0.3 to 3 m in height, but generally grows to just above the crop in which it is growing. It is a prolific seed producer with 17,000 seeds per plant being produced on average. The seeds can persist in the soil for up to 50 years and are unaffected by passage through animals or by ensilement.

Velvetleaf is widely distributed throughout most of the United States and much of southeastern Canada. It is considered as one of the most common and costly weeds in the North Central region of the United States. This weed species occurs in waste places, vacant lots, gardens and cultivated fields. Velvetleaf is a serious weed problem in corn, soybeans, cotton, wheat, oats, barley, sugarbeets, sunflower, tomato and other cultivated crops. Infestations of this weed presently cause significant yield reductions in these crops and the problem is increasing due to the prolific seed production of velvetleaf and the difficulty in the control thereof.

In most cropping systems, chemical herbicides have been developed to provide acceptable to excellent control of many grass and broadleaf weeds. However, widespread and continuous use of certain herbicides has favored the establishment of problem, difficult to control weeds such as velvetleaf. A combination of chemical herbicides and cultivation are presently used to control velvetleaf populations in various crops, but these methods are inadequate for the control of velvetleaf as infestations of this weed are continuing to increase in size and in number. Problems with cultivation for the control of velvetleaf include:

1. appropriate timing to avoid injury to the crop plants is difficult;
2. lack of control of late germinating plants;
3. it cannot be used in new cropping systems such as solid seeded soybeans (SSS).

The problems associated with the present chemical herbicides for velvetleaf control include:

1. lack of soil persistence resulting in no control of late germinating velvetleaf;
2. most chemical herbicides cause some detrimental effects to the growth of the crop;
3. chemical herbicides may adversely affect non-target organisms;
4. toxic residues of chemical herbicides may persist in the environment or contaminate our food.

Dingley, J. M. and Gilmour, J. W., New Zeal. J. For. Sci. 2(2): 192 (1972) discloses the *C. coccodes* (Wallr.) Hughes fungus in order to distinguish it from the *C. acutatum*, to which the studies refer. Stevenson, W. R., Evans, G. E., and Barksdale, T. H., Pl. Dis. Rept. 62(11): 937 (1978) discloses the losses in fresh market tomato crops produced by anthracnose disease caused by *C. coccodes* (Wallr.) Hughes among others, and the development of tomato cultivars with genetic resistance to the disease.

Although many patents deal with the fungal control of vegetation, none of them disclose the use of *Colletotrichum coccodes* (Wallr.) Hughes for this treatment. Such patents include the following:

| U.S. Pat. Nos.: | |
|---|---|
| 3,087,865 | Drake et al |
| 3,300,390 | Tiner et al |
| 3,308,038 | Rhodes et al |
| 3,150,062 | Greenberg et al |
| 3,357,895 | Cherry |
| 3,361,555 | Herschler |
| 3,999,973 | Templeton |
| 4,061,488 | Mann |
| 4,162,912 | Charudattan |
| 4,390,360 | Walker |

SUMMARY OF INVENTION

In a broad aspect, the present invention relates to a process for controlling undesirable vegetation by appling *Colletotrichum coccodes* spores onto the undesirable vegetation or onto the situs of the undesirable vegetation.

The preferred composition which is used in the process according to the invention comprises *Colletotrichum coccodes* spores in an agricultural carrier preferably having a spore concentration of $1 \times 10^7$ to $1 \times 10^9$ spores per ml of carrier.

The process according to the invention is especially useful for the control of velvetleaf (*Abutilon theophrasti*) which involves the application of a spore suspension of a fungus, *Colletotrichum coccodes* which results in a debilitating disease of velvetleaf. The fungal spore application provides a unique narrow spectrum herbicide for the control of a single noxious weed species, velvetleaf in soybeans, corn and other crops.

The preferred agricultural carrier comprises water, with or without 1% by weight gelatin, the spores being uniformly dispersed in the carrier.

The spore containing composition is preferably applied at the cotyledon to 6-leaf stage of velvetleaf, and under warm and moist conditions. The composition may be applied onto the leaf surface of the velvetleaf.

DESCRIPTION OF PREFERRED EMBODIMENTS

The organism, *C. coccodes* has been deposited and can be obtained from the permanent collections of the Biosystematic Research Institute Agriculture Canada, Ottawa, Canada where it has been deposited under an unrestricted deposit as *C. coccodes* DAOM 182826.

The fungus produces necrotic spots (lesions) on the leaves of velvetleaf which coalesce and cause the death of leaves and stems. When the fungus infects young velvetleaf plants, a devastating blight develops and most diseased plants are killed.

*C. coccodes* can be grown on solid or in liquid media for spore production. Media can be potato dextrose, malt extract, V-8, or beef extract. For production of larger quantities of spores liquid media is used. For example:

| Formula I - Modified Beef Extract | |
|---|---|
| dextrose | 10.67 g |
| nutrient broth | 10.69 g |
| peptone | 0.44 g |
| distilled water (to make) | 1000 ml |
| Formula II - Richard's Modified V-8 Medium | |
| sucrose | 10.00 g |
| KNO$_3$ | 10.00 g |
| MgSO$_4$.H$_2$O | 2.50 g |
| KH$_2$PO$_4$ | 5.00 g |
| FeCl$_3$ | 0.02 g |
| V-8 juice | 150 ml |
| distilled water (to make) | 1000 ml |

Liter flasks containing 500 ml of the liquid media are inoculated with spores and incubated at 28° C. with occasional agitation for 5 to 10 days. The contents of the flasks are then filtered to remove fungal mycelium. The remaining liquid containing the fungal spores is centrifuged in a refrigerant centrifuge. The supernatant is discarded and the spore concentrate is collected and stored at 4° C. prior to application.

The spore concentrate is mixed with an agriculturally acceptable diluent or carrier for application to the target weed, such as velvetleaf. The preferred carrier is water containing 1% gelatin and the spore concentrate is uniformly dispersed in the carrier. The spore suspension (formulation) is sprayed onto the leaf surface of the undesirable vegetation at a preferred rate of $10^7$ to $10^9$ spores per m$^2$ in 47 to 187 ml of water per m$^2$.

The velvetleaf isolate of *C. coccodes* does not damage soybean, corn, and other crop plants and can be used in these crops to control velvetleaf. The preferred application is at the cotyledon to 6-leaf stage of velvetleaf with the associated environmental conditions being warm and moist. Repeat applications of the spore formulation may be required and control is improved if the growth of the associated crop is vigorous.

The invention will now be illustrated by means of the following non-limiting examples.

EXAMPLE 1. GROWTH CHAMBER STUDIES

Cultures of *C. coccodes* are grown on malt agar in petri dishes and when the cultures are sporulating, small portions of the agar (about 1 cm$^3$) are removed and used for inoculation of culture flasks. 250 ml flasks containing 75 ml of modified beef extract media are aseptically inoculated with an agar cube. Flasks are incubated on a rotary shaker (250 rpm) at 20° to 25° C. for 5 to 10 days. The cultures are then filtered to remove mycelia, the remaining liquid containing the spores is centrifuged in an IEC B20A refrigerated centrifuge (870 rotor) at 7000 rpm for 20 minutes. The spore concentrate is resuspended in distilled water to reach a final spore concentration of $1 \times 10^7$ spores per ml. Velvetleaf plants growing within controlled environment chambers are inoculated by spraying the spore suspension onto the plant surface until runoff occurs.

Optimum conditions for spore germination, infection and disease development were determined. Warm temperatures and free moisture are required for spore germination and infection of host plant material. These processes occur best when temperatures are 24° to 30° C. and when a saturated atmosphere is maintained for 8 to 24 hours. After infection occurs higher temperatures accelerate disease development with 30° C. night and 35° C. day temperatures being optimum. All growth stages tested (cotyledon to the 12-leaf stage) were equally susceptible to infection.

EXAMPLE 2. FIELD STUDIES

A. Spore preparation

Cultures of *C. coccodes* are grown on PDA plates for 1 to 2 weeks. When cultures are sporulating, spores are aseptically suspended in 10 ml of sterile water by swirling. Spore suspension is then transferred to 1 L flasks containing 500 ml of Richard's Modified V-8 medium. Cultures are then incubated at 28° C. for 6-9 days with occasional swirling. Spores are harvested by filtration through 2 layers of cheesecloth followed by centrifugation in 250 ml bottles in a Beckman JA-14 rotor at 4,000 RPM for 15 minutes at 15° C. Pellets of spores are resuspended in distilled water and rinsed twice with distilled water followed by centrifugation each time. Spores are then stored at 4° C. Yields exceed $6 \times 10^9$ spores per liter of growth media used.

B. Formulation and application

Spores are resuspended in 1% gelatin concentration and are adjusted to apply $10^7$ or $10^9$ spores per m$^2$ in 47, 94, or 187 ml per m$^2$.

C. Field control for velvetleaf

When one application of spores is applied under warm field conditions, velvetleaf biomass is reduced by 85% as compared to unsprayed control within 3 weeks after spraying. The fungus spreads from infected foliage to surviving foliage or new growth and suppresses velvetleaf growth for the rest of the growing season.

What is claimed is:

1. A process for selectively controlling velvetleaf, *Abutilon theophrasti*, in a field comprising an agricultural plant, said process comprising applying an amount of *Colletotrichum coccodes* DAOM 182826 spores onto said velvet leaf or onto the situs of said velvetleaf, said amount being effective to control velvet leaf, where said agricultural plant consists essentially of corn, soybean, cotton, wheat, oats, barley, sugar beets, sunflowers or tomatoes.

2. The process of claim 1, comprising applying onto said velvetleaf or onto said situs of said velvetleaf a composition comprising *Colletotrichum coccodes* DAOM 182826 spores in an agricultural carrier having a spore concentration of $1 \times 10^7$ to $1 \times 10^9$ spores per ml of carrier.

3. The process of claim 2, wherein said agricultural carrier comprises water, said spores being uniformly dispersed in said carrier.

4. The process of claim 2, wherein said agricultural carrier comprises water containing 1% per weight gelatin, said spores being uniformly dispersed in said carrier.

5. The process of claim 2, wherein said spore containing composition is applied at the cotyledon to 6-leaf stage of velvetleaf.

6. The process of claim 5, wherein the application is carried out under warm and moist conditions.

7. The process of claim 4, comprising spraying said spore containing composition onto the leaf surface of said velvetleaf.

8. The process of claim 7, comprising spraying said composition at a rate of $10^7$ to $10^9$ spores per $m^2$ in 47 to 187 ml of water per $m^2$.

9. An agricultural composition for selectively controlling velvetleaf, *Abutilon theophrasti*, comprising *Colletotrichum coccodes* DAOM 182826 dispersed in an agricultural carrier at a concentration of from $1 \times 10^7$ to $1 \times 10^9$ spores per ml of agricultural carrier.

10. The agricultural composition of claim 9, wherein said agricultural carrier comprises water, said spores being uniformly dispersed in said carrier.

11. The agricultural composition of claim 9, wherein said agricultural carrier comprises water containing 1% by weight gelatin, said spores being uniformly dispersed in said carrier.

* * * * *